United States Patent [19]

Sauter et al.

[11] Patent Number: 4,965,089

[45] Date of Patent: Oct. 23, 1990

[54] METHOD AND APPARATUS FOR THE GELATIN COATING OF CAPLETS

[75] Inventors: Erich W. Sauter, Washington Crossing; John Hamburg, Fallsington; Warren L. Phillips, Southampton, all of Pa.

[73] Assignee: Sauter Manufacturing Corp., Hulmeville, Pa.

[21] Appl. No.: 336,006

[22] Filed: Apr. 10, 1989

[51] Int. Cl.⁵ .............................................. A61K 9/00
[52] U.S. Cl. .......................................... 427/3; 118/30; 118/503; 424/451; 424/463
[58] Field of Search ...................... 427/3; 118/30, 503; 424/463, 451

[56] References Cited

U.S. PATENT DOCUMENTS

| | | |
|---|---|---|
| 299,785 | 6/1884 | Herrington et al. |
| 540,538 | 6/1895 | Colton. |
| 542,611 | 7/1895 | Holbrook. |
| 599,865 | 3/1898 | Richards. |
| 724,436 | 5/1903 | Clark. |
| 961,936 | 6/1910 | Colton et al. |
| 1,416,796 | 5/1922 | Davis. |
| 1,787,777 | 1/1931 | Colton. |
| 2,373,721 | 4/1945 | Taylor et al. |
| 2,410,110 | 10/1946 | Taylor. |
| 2,596,176 | 5/1952 | Scherer ............................ 117/43 |
| 2,671,245 | 3/1954 | Kath .................................. 18/25 |
| 2,727,473 | 12/1955 | Wolff et al. ...................... 107/1 |
| 2,853,421 | 9/1958 | Adams et al. .................. 167/82 |
| 2,997,018 | 8/1961 | McGraw, Jr. ................. 118/612 |
| 3,045,641 | 7/1962 | Oddo ................................ 118/16 |
| 3,141,792 | 7/1964 | Lachman et al. ............... 118/6 |
| 3,185,626 | 5/1965 | Baker ............................. 167/82 |
| 3,275,519 | 9/1966 | Glassman ....................... 167/82 |
| 3,431,338 | 3/1969 | Munzel ........................... 424/21 |
| 3,573,966 | 4/1971 | Hostetler ...................... 117/100 |
| 3,607,364 | 9/1971 | Lopez et al. ................ 117/100 A |
| 3,896,762 | 7/1975 | Banker ............................ 118/30 |
| 3,991,225 | 11/1976 | Blouin .............................. 427/3 |
| 4,118,522 | 10/1978 | Stellmach ........................ 427/3 |
| 4,129,666 | 12/1978 | Wizerkaniuk ................... 427/3 |
| 4,238,510 | 12/1980 | Cherukuri et al. .............. 426/5 |
| 4,407,844 | 10/1983 | Melliger .......................... 427/3 |
| 4,581,242 | 4/1986 | Forster ............................. 427/3 |
| 4,670,287 | 6/1987 | Tsuji ................................. 427/3 |
| 4,705,695 | 11/1987 | Lehmann et al. ............... 427/3 |
| 4,725,446 | 2/1988 | Forster et al. ................... 427/3 |
| 4,820,524 | 4/1989 | Berta .......................... 427/3 X |

FOREIGN PATENT DOCUMENTS 100146 6/1936 Australia.

OTHER PUBLICATIONS

Berta, Norbert I., Gelatin Coated Caplets and Process for Making Same, Aug. 24, 1988, European Patent Application, Entire Article. #0 279 682.

Primary Examiner—Michael Lusignan
Attorney, Agent, or Firm—Mathews, Woodbridge & Collins

[57] ABSTRACT

A caplet dipping machine includes a caplet holding plate including sets of caplet gripping collets on both sides thereof so that caplets can be dipped on one end, pushed through the plate and dipped at the other end. The collets on one side are mounted back-to-back with the collets on the other side in apertures formed in the holding plate. Caplets are fed into the collets on one face of the holding plate by a loading plate which receives the unfinished caplets from a hopper. A plurality of loading transfer pins push the caplets through the first set of collets to the second set of collets on the bottom face of the holding plate. The caplets are then dipped in a first gelatin bath, flipped by a first plate flipping mechanism and dried in a first drying section. The caplets are next pushed through from the second set of collets back to the first set of collets by a second set of transfer pins before passing through a second gelatin dipping bath. A second plate flipping mechanism then inverts the plate for a second time and the plate proceeds from there through a second drying section. A third, or exit, transfer means then pushes the finished product into a receiving bin. An improved coat is also achieved by the use of a pair of annular gelatin holding pans through which gelatin continuously flows under the influence of an impeller located between the pans. It is possible for the apparatus to operate at high speeds and high efficiencies due to the large capacity of the plates and the clean, open architecture of the system.

11 Claims, 10 Drawing Sheets

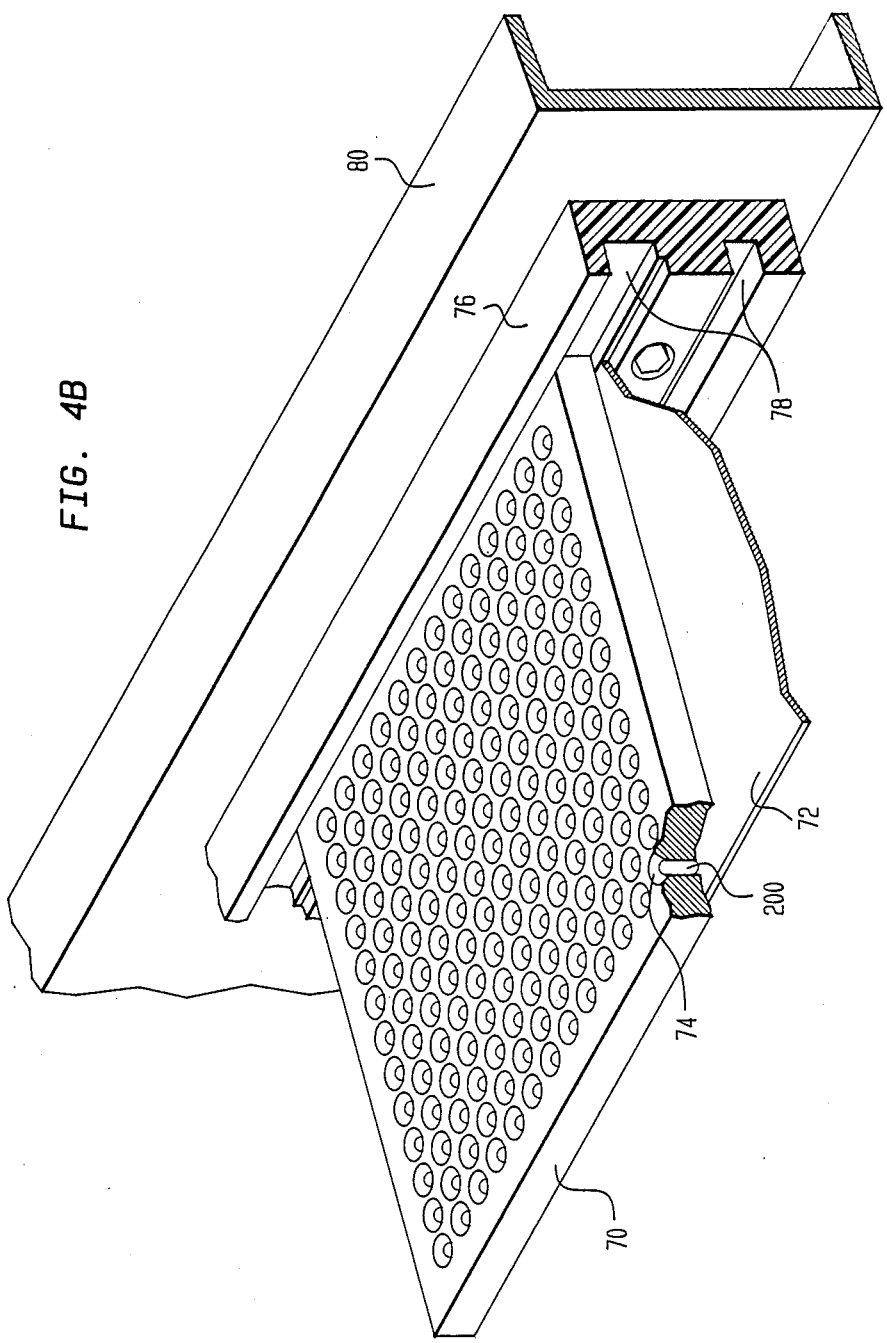

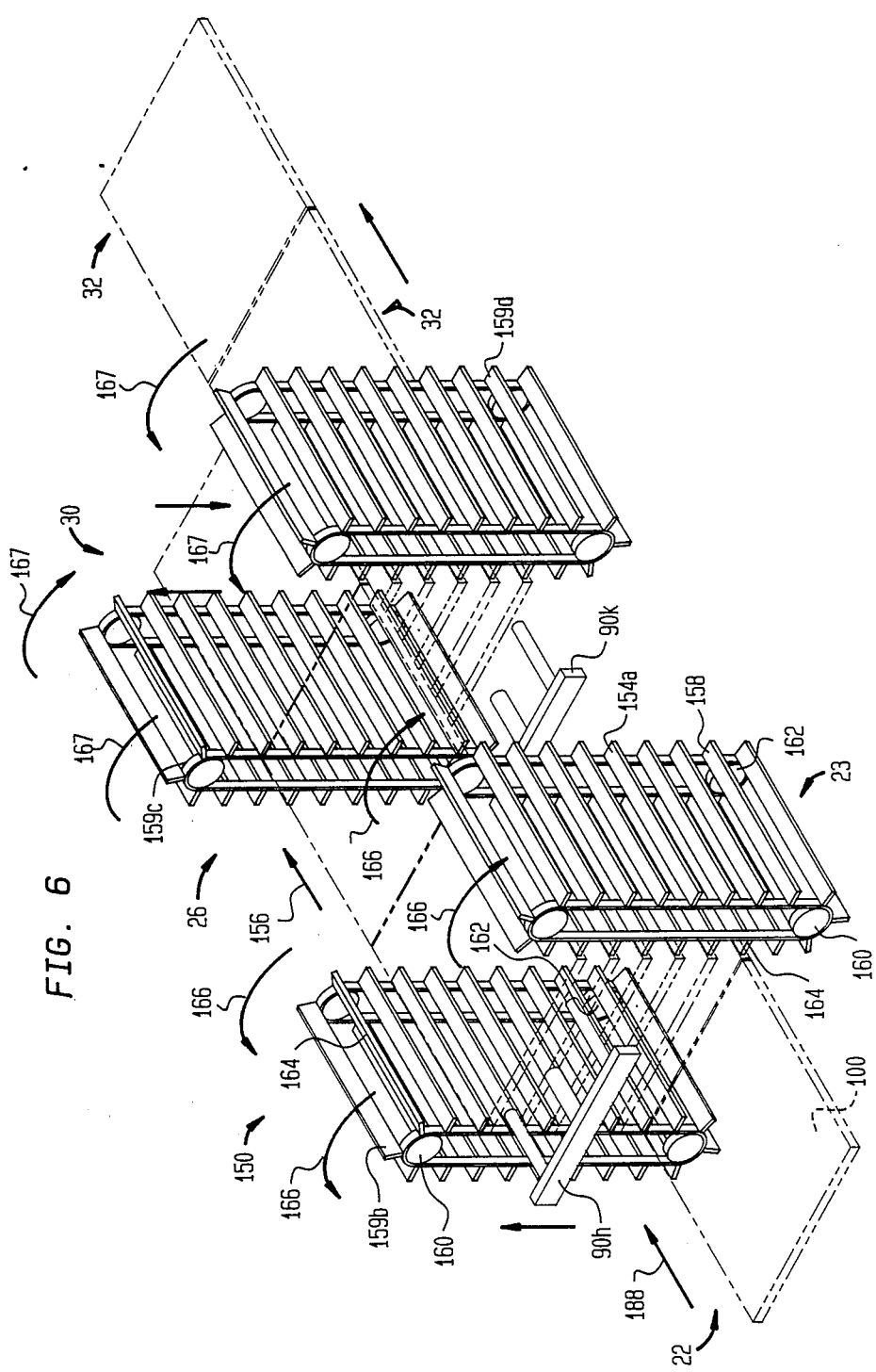

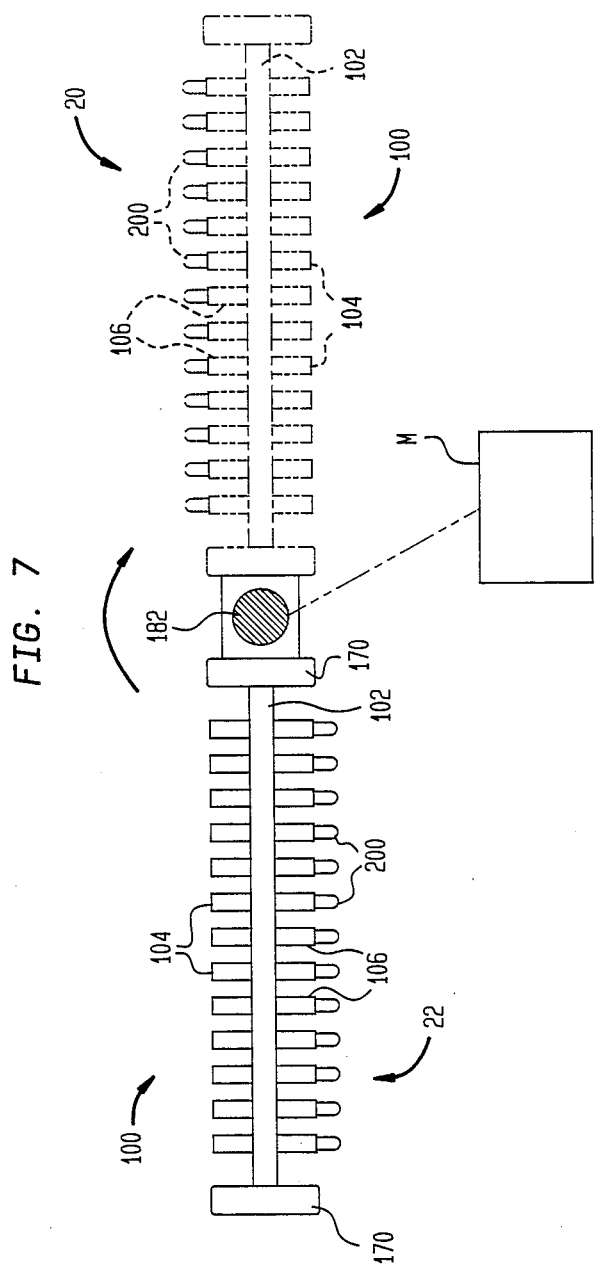

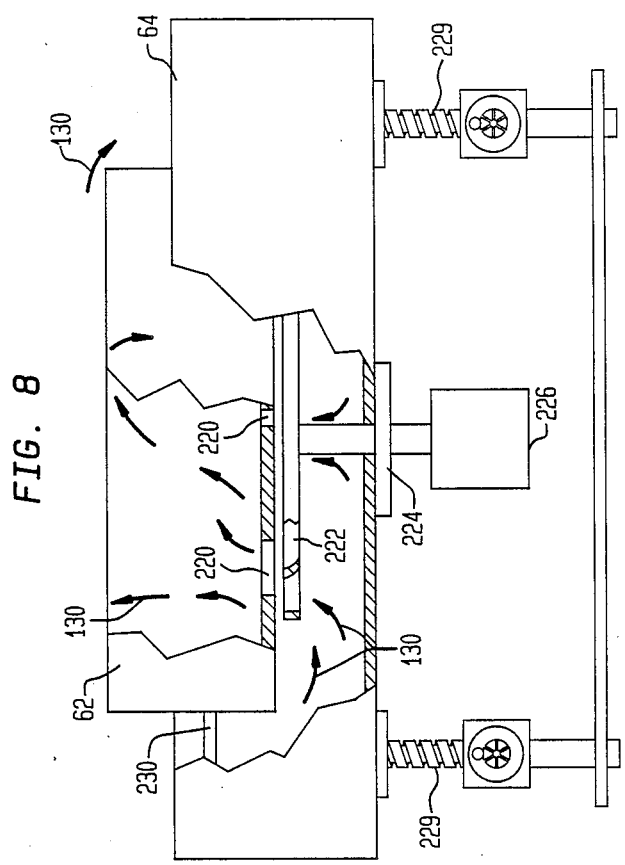

METHOD AND APPARATUS FOR THE GELATIN COATING OF CAPLETS

BACKGROUND OF THE INVENTION

1. Field of the Invention

The invention relates to a method and apparatus for coating caplets with gelatin.

2. Background of Related Art

The concept of coating tablets or caplets with gelatin is known in the prior art. Pills or tablets having gelatin coatings are described in the patent literature, for example see U.S. Pat. Nos. 2,410,110 or 3,275,519.

There appear to be two primary methods of applying a gelatin coating to a pill. The first method is to hold the pill or tablet during the dipping process. The second method is to spray a coating over the pill as it tumbles. U.S. Pat. No. 599,865 issued Mar. 1, 1898 discloses an early system in which a pill is held at one end by bees wax in a holder while its other end is dipped. The pills are then transferred in such a way as to hold the previously dipped end while the non-dipped end is then coated with gelatin.

A machine for dipping capsules while holding the same by means of a vacuum above a gelatin filled pan is described in U.S. Pat. No. 540,538 issued on June 4, 1895 to A. Colton.

Other methods for providing a coat to a pill are also described in the following U.S. Pat. Nos.: 2,853,421; 3,185,626; 3,431,338; 3,607,364; 4,670,287; 4,705,695 and Australian Pat. No. 100,146 accepted June 19, 1937.

Patents which disclose the technique of coating a tablet with gelatin or similar substance by either spray-coating or immersing the tablet in a bath are disclosed by the following references: U.S. Pat. Nos. 1,416,796; 3,141,792; 3,573,966; 3,991,225; 4,118,522; 4,129,666; 4,581,242 and 4,725,446.

U.S. Pat. No. 2,373,721 is of interest in that it discloses an apparatus for coating small objects such as pills, tablets and the like with gelatin. The tablets are held in place by suction while they are coated. Other mechanisms of possible relevance include the disclosures in the following U.S. Pat. Nos.: 229,785; 542,611; 2,596,176; 2,727,473; 2,997,018 and 4,407,844. Other U.S. Patents of possible interest include U.S. Pat. Nos. 724,436; 3,045,641; 3,896,762 and 4,238,510.

A recent interest has been shown in the concept of coating a caplet with gelatin. Such products are known as "gelcaps". A method and apparatus presently used to coat caplets is described in European Pat. Application No. 0 279 682 published on Aug. 24, 1988. According to that document, a caplet is held in a collet which in turn is held in an elongated bar. The bar is similar to a pin bar on a typical Colton Model 950 gelatin capsule making machine. The caplet is dipped in the dipping pan and then dried. It is subsequently brought into alignment with another elongated bar and the caplet is transferred from one bar to the other by means of a pin. The other side of the caplet is then dipped and forced out by the incoming caplet.

The foregoing mechanism is relatively inefficient because it requires the modification of an existing Model 950 Colton gelatin capsule machine or its equivalent. The machine can only operate on one row of caplets at a time. However, the machine is able to take advantage of some of the features that preexisted on the original Colton machine.

It has been found, however, that the speed of the converted Colton machine is relatively slow and the process requires many steps, some of which are left over from the original gelatin capsule making process.

It is interesting to note that the late Arthur Colton, the founder of the company that makes the Model 950 Colton gelatin capsule machine, had himself invented a machine for dipping tablets and gelatin. The invention is described in U.S. Pat. No. 540,538 entitled MACHINE FOR DIPPING PILLS and issued on June 4, 1895. The machine described in U.S. Pat. No. 540,538 holds pills in a tray by suction while the pills are dipped in a bath of liquid gelatin.

The general concept of holding a tablet or caplet in a split collet and then ejecting same with a rod is a technique that already exists on non-converted Model 950 Colton gelatin capsule machines. The same technology is also described in the prior art patent literature. For example, U.S. Pat. No. 2,671,245 entitled CAPSULE MACHINE and issued to A. W. Kath on Mar. 9, 1954 and assigned to Eli Lilly & Co., Indianapolis, Ind. shows the general state of the art. Gelatin caps or bodies are formed by dipping rods into a bath of liquid gelatin and permitting them to dry. After the gelatin caps or bodies have dried, they are stripped off into holding collets. One set of collets holds the capsule bodies and another parallel set of collets holds the capsule caps. Rods passing through the center of the collets push the gelatin caps and bodies towards each other in a mating plate where they form an empty gelatin capsule.

A similar machine is described in U.S. Pat. No. 1,787,777 issued to A. Colton and entitled Capsule Machine published on June 6, 1931. The patent is noteworthy again for the showing of the holding of a capsule-like body in a split collect chuck prior to assembly as a complete gelatin capsule. Another more advanced version of the same type of invention is described in U.S. Pat. No. 2,373,721 entitled Apparatus for Coating.

Similarly, note U.S. Pat. No. 961,936 issued on June 21, 1910 to A. Colton and B. W. Scott and entitled Machine for Making Capsules. This patent also shows the early state of the art with reference to the concept of holding a capsule-like body in a chuck having the characteristics of a collet.

Lastly, U.S. Pat. No. 2,727,473 entitled Coating Mechanism issued to J. E. Wolff et al. on Dec. 20, 1955 describes an invention in which tablets are coated on both top and bottom while held in a receiver and manipulated up and down.

The inventors have discovered that they can substantially improve upon the speed, efficiency and quality of the product in the manner set forth below.

SUMMARY OF THE INVENTION

Briefly described the invention comprises a method and apparatus for dipping caplets in which the caplet is held in a unitary split collet holding plate which includes caplet gripping collets on both sides thereof so that the caplets can be dipped on one end, pushed through the plate and dipped on the other end.

Initially, caplets are fed into a caplet loading plate separated from the unitary split collet holding plate by a doctor plate. A pusher mechanism moves both the unitary holding plate and the caplet loading plate past the doctor plate so that the caplets fall directly onto the collets. The caplets are then pushed through the collets on the upper side of the holding plate, through the center of the holding plate, and out to the ends of the second set of collets on the bottom of the holding plate until they emerge on the bottom side. The holding plate, with the caplets held in the bottom set of collets, advances through a first gelatin dipping station where it is coated with liquid gelatin. The gelatin dipping station includes an inner circular pan where the liquid gelatin is kept and an outer pan which absorbs the overflow. An impeller in the outer pan forces liquid gelatin to flow through and over the edges of the inner pan so as to keep the gelatin in constant circulation. The caplet holding plate then advances to a first flipper station where it is turned over. The capsules are now facing upwards and advance through a first drying tower. The holding plates initially travel upward through a hot, dry countercurrent and then when they reach the top travel downward and are subsequently moved toward a transfer station where a second set of caplet pushpins pushes the caplets from the first upward facing set of collets, through the plate body and down to the second set of downward facing collets so that the non-dipped ends of the caplets now face downward. The previously un-dipped caplet portions are then passed through a second liquid gelatin dipping station, similar to the first liquid gelatin dipping station and then flipped over, in a turn-over similar to the first turnover so that the dipped portion of the caplet is facing upward. The holding plate then advances to the input of a second drying tower similar to the first drying tower. The dried caplets in their holding plates emerge from the second drying tower and advance toward the caplet fill station, from where it began. Right before the holding plate reaches the caplet fill station, a third set of caplet pusher pins pushes the caplets, which have now been dipped and dried on both sides, completely out of their holding collets into a collection bin. The empty holding plate then advances into position under the caplet loading station and the process starts again from the beginning.

There are four 90° transfer stations at each corner of the apparatus and, accordingly, the layout of the system is in the form of a rectangle and the holding plates travel around in a circuit having the same shape. The caplet loading plates travel in a smaller rectangle within the major rectangle. After the caplet holding plate has been initially loaded and indexed by one unit, the upper loading plate is indexed at 90° from the caplet holding plate, moved forward by three stations, and then indexed at 90° again to bring it back into synchronization above an empty caplet holding plate before it enters the caplet loading station.

The invention can be further understood by reference to the following drawings.

BRIEF DESCRIPTION OF THE DRAWINGS

FIG. 4B is a partial perspective cut-away view of a loaded caplet loading plate directly above the doctor plate.

FIG. 6 is a perspective schematic view of the up and down elevator sections of the first and second drying towers.

FIG. 7 is an end view of a portion of the device showing the flipping action.

FIG. 8 is an elevation partly broken away, of the dipping apparatus.

DETAILED DESCRIPTION OF THE PREFERRED EMBODIMENT

During the course of this description, like numbers will be used to identify like elements according to the different Figures which illustrate the invention.

Figure 1:
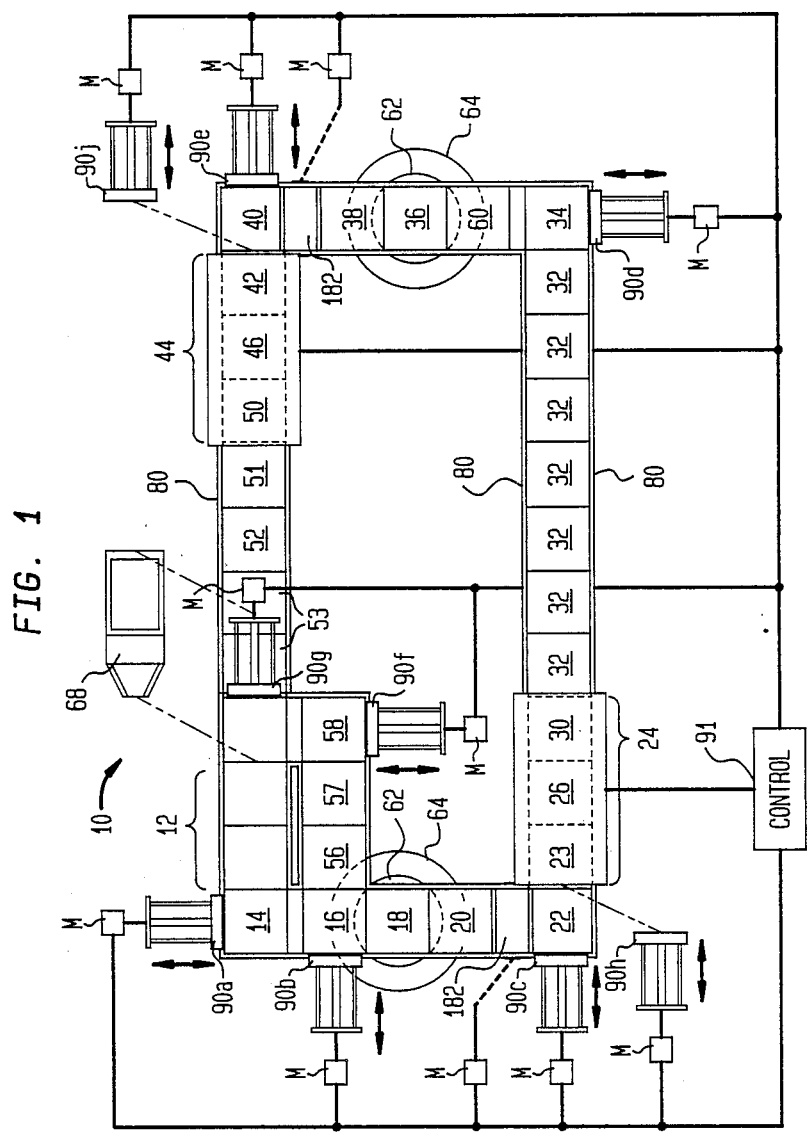
FIG. 1 is a schematic top plan view of the preferred embodiment of the caplet coating apparatus.
Figure 2:
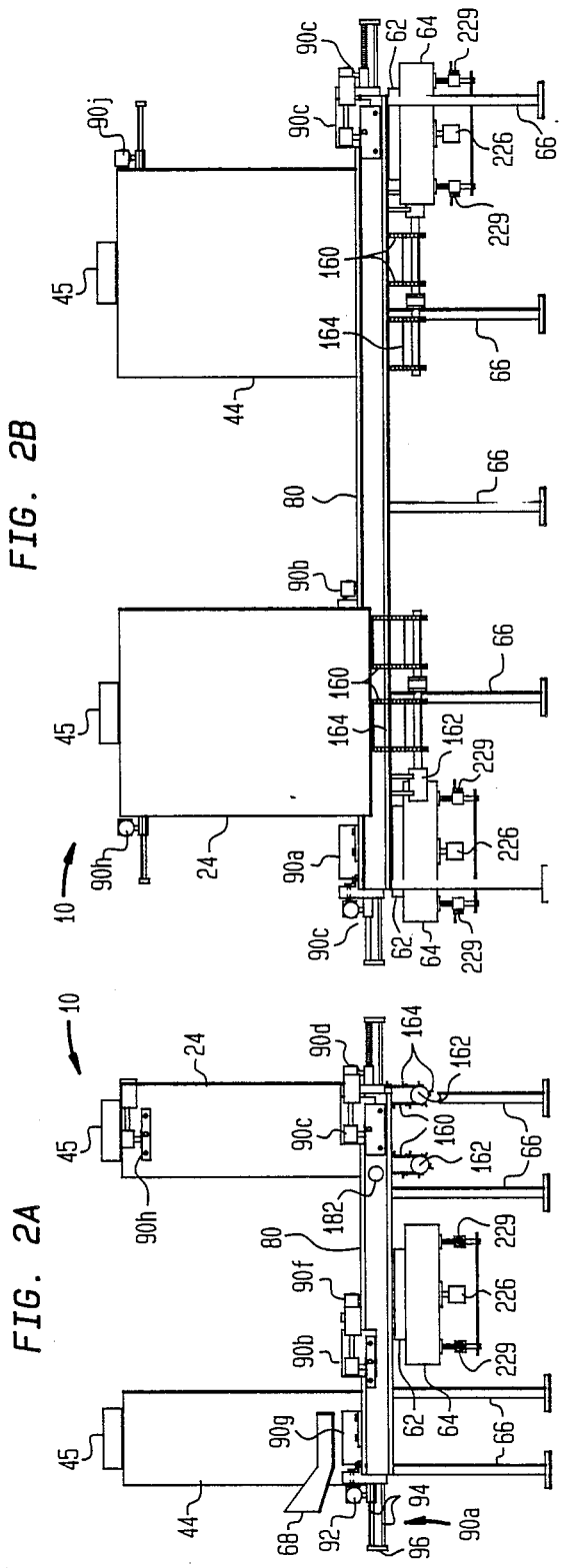
FIG. 2A is an end elevational view of the apparatus illustrated in FIG. 1.
FIG. 2B is a side elevational view of the apparatus illustrated in FIG. 1.

The layout of the preferred embodiment 10 of the invention is shown in top plan view in FIG. 1. FIGS. 2A and 2B illustrate the same apparatus as seen from the end and the side thereof, respectively.

Figure 4A:
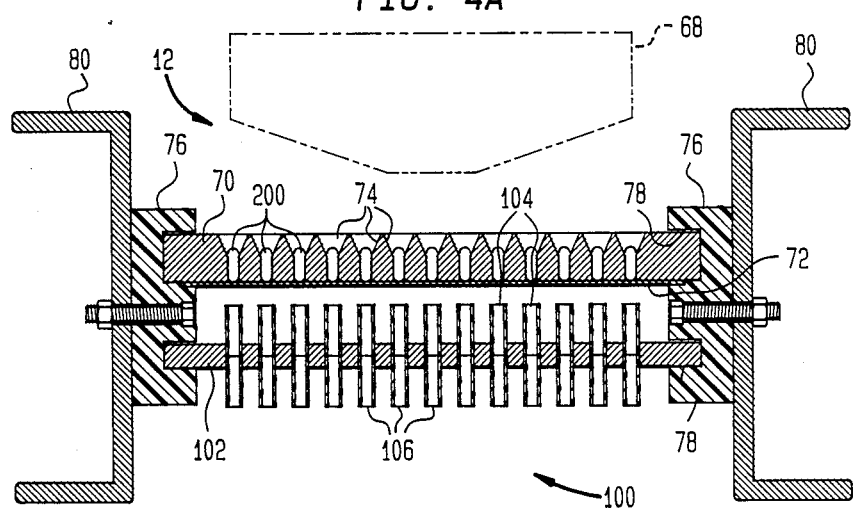
FIG. 4A is a cross-sectional view of a loaded caplet loading plate, directly above a unitary split collet caplet holding plate separated therefrom by a doctor plate.

Initially, undipped caplets 200 are dumped into caplet feed hopper 68 located directly above a caplet loading plate 70 at loading station 12. Loading station 12 is shown in FIG. 1 to be of a length equal to three loading plates 70. When at station 12, caplet loading plate 70 is located directly above a stationary doctor plate 72 which prevents the caplets 200 from dropping through the apertures 74 in the loading plate 70 (FIG. 4A). Apertures 74 have a funnel-shaped opening that assists the caplets 200 into their position directly above doctor plate 72. As shown in FIG. 4A, the loaded caplet loading plate 70 and doctor plate 72 are positioned directly above the unitary split collet caplet holding plate 100. Both the loading plate 70 and the caplet holding plate 100 are slidably held in grooves 78 in blocks 76 mounted to the frame 80 of the machine having legs 66. Doctor plate 72, however, is permanently attached to blocks 76 so that it cannot move. Therefore, loading plate 70 and caplet holding plate 100 can move in unison in the groove 78 in block 76, whereas the doctor plate 72 is relatively stationary.

Figure 3:
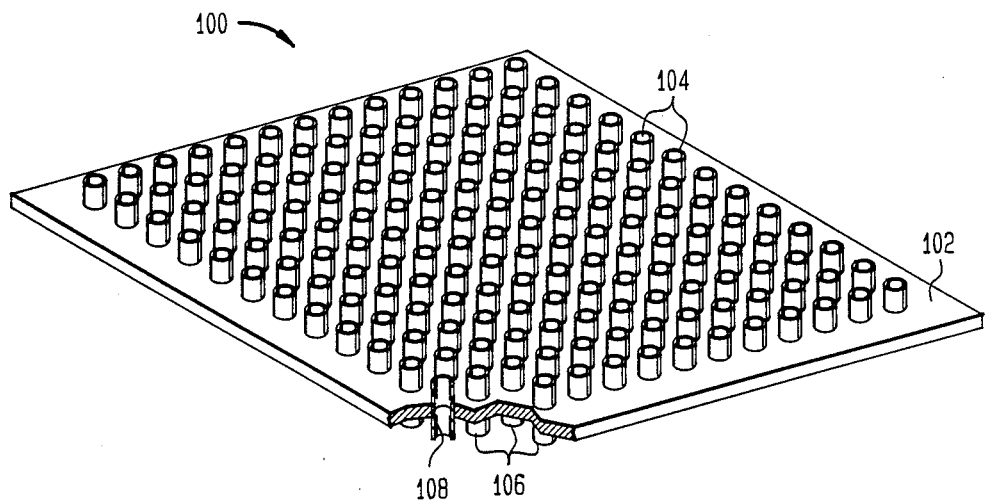
FIG. 3 is a perspective partial cut-away view of a unitary, split collet caplet holding plate.

The unitary split collet caplet holding plate 100 includes a body section 102 that supports a first set of split collets 104 located on a first side of plate 102 and a second set of split collets 106 attached to the second surface of plate 102 in back-to-back relationship. Collets 104 and 106 each share a common aperture 108 that also passes through the plate body 102. The structure of the caplet holding plate 100 is shown in detail in FIG. 3. The collets 104 and 106 are identical, each having the ends thereof longitudinally split to form four resilient fingers. The inside diameter of each collet 104 and 106 at the open end, is slightly smaller than the inside diameter of the collet at the butted ends. As such, the collets 104 and 106 are dimensioned so that the resilient fingers may grip the caplets 200 and permit the caplets 200 to be forced therethrough.

Figure 5A:
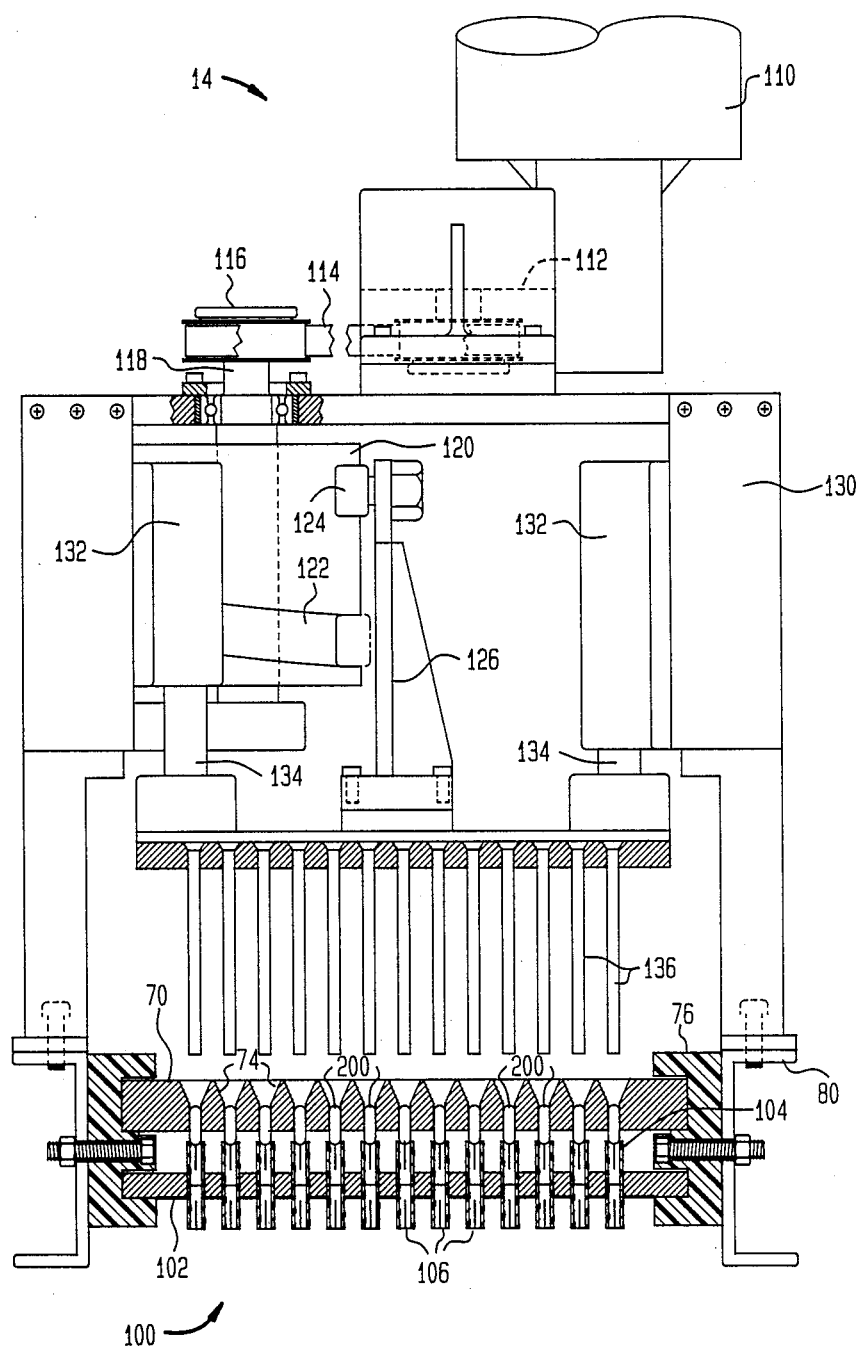
FIG. 5A is an elevational view, partly in cross-section, illustrating the caplet pushpin and load mechanism with the pushpins in position directly above the loaded caplet loading plate which in turn is located directly above the unitary split collet caplet holding plate.
Figure 5B:
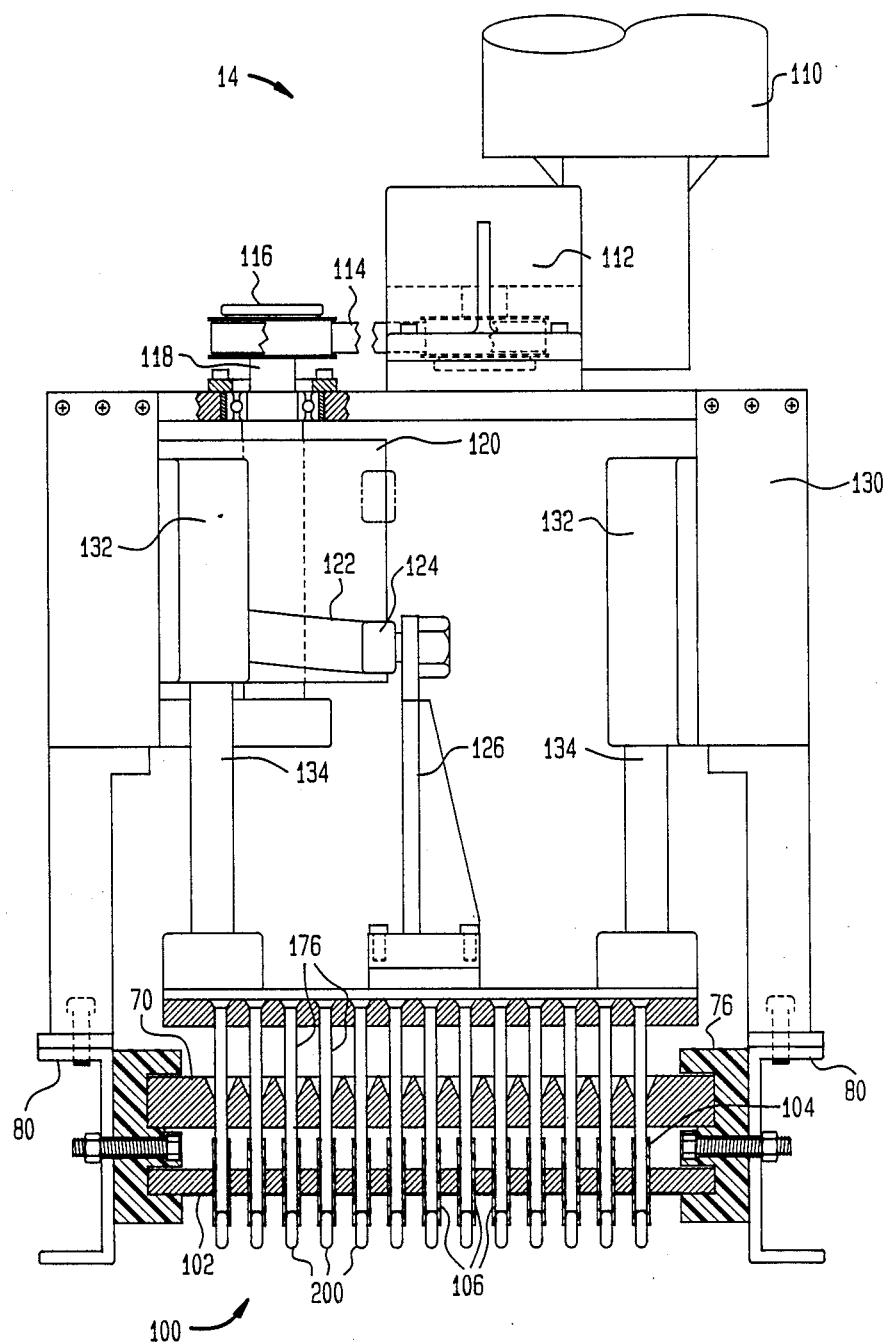
FIG. 5B is an elevational view illustrating the pushpin loading mechanism of FIG. 5A in cross-sectional detail with the caplets pushed through to the bottom set of split collets in the unitary split collet caplet holding plate.
Figure 5C:
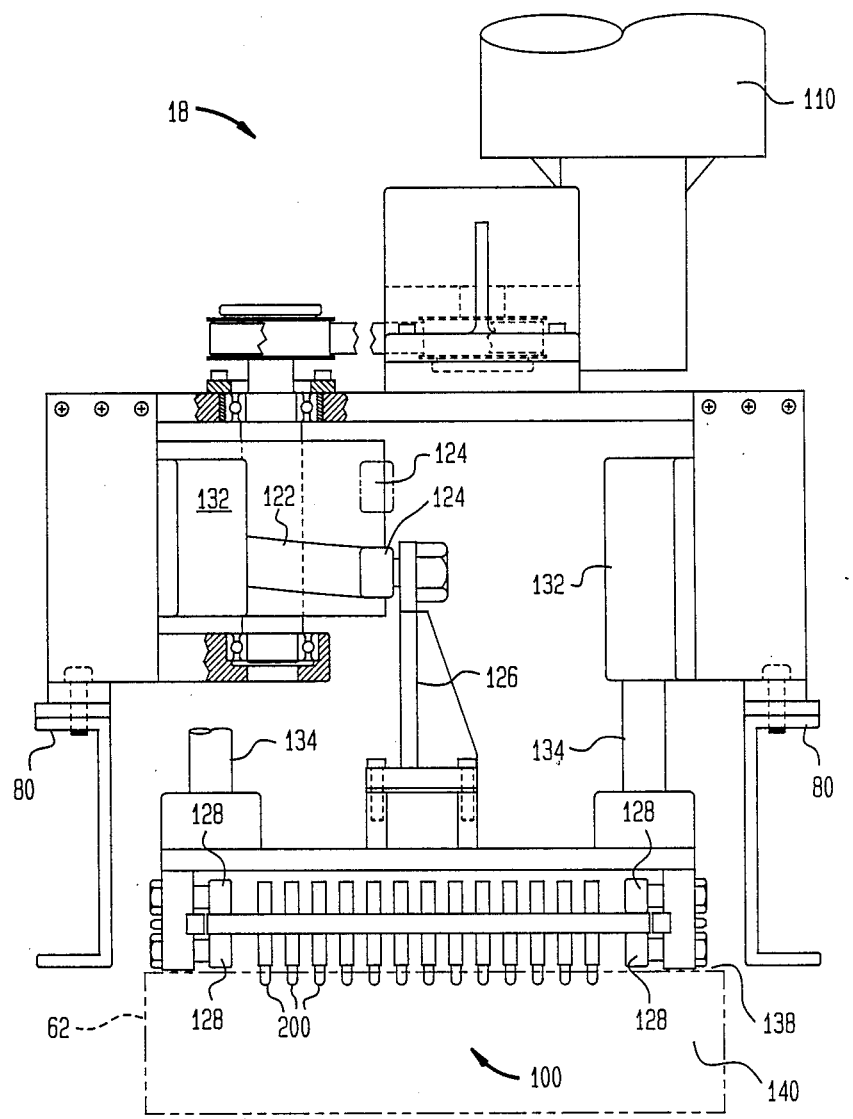
FIG. 5C is an elevational view of a portion of the mechanism showing the caplets being dipped.

FIG. 4A illustrates the loaded caplet loading plate 70 while at station 12 and in position directly above an empty caplet holding plate 100 after the loading plate 70 has been loaded by the caplet feed hopper 68 but before the caplets are transferred by the mechanism illustrated in FIGS. 5A-5C. Plates 70 and 100 move easily in blocks 76 which may be made from simple plastics. A plurality of pushers 90a-90k are employed to move plates 70 and 100. The pusher drive device preferably comprises a commercial 230 volt single phase one-quarter horsepower motor M having an encoder so that the related pusher mechanism can be controlled by a conventional microprocessor control 91, shown connected to each motor M, to determine and control the stroke of the pushers 90a-90k. Control 91 could alternatively be a conventional timing switch that simply operates relays in the appropriate sequence to energize the motors M connected thereto.

After the loading plate 70 has been loaded with caplets 200 and positioned above the caplet holding plate 100 as shown in FIG. 4A and 4B, plates 70 and 100 are then pushed into position to station 14. At this point, there will be a series of three plates 70 in station 12. Pusher 90g will push on the series of plates 70 and advance these plates one plate length such that a loaded plate 70 will be advanced to station 14. During this pushing operation, the caplets 200 will be randomly falling into apertures 74 of the other two plates in station 12. When the pusher 90g is withdrawn, an empty space will be left in station 12, permitting pusher 90f to push an unloaded plate 70 therein from station 58. Simultaneiously, pusher 90e will be energized by control 91 to push the series of holding plates 100 such that an empty holding plate 100 is also advanced to station 14. In this way, superimposed plates 70 and 100 are simultaneiously moved into station 14 where the caplets 200 are permitted to fall partially from apertures 74 and rest on the resilient fingers of collets 104. Station 14 comprises the first pushpin station and the first 90° turn station as illustrated in FIG. 5A. The first pushpin station 14 is similar in structure to the second pushpin station 34 and the exit pushpin station 52.

The first capsule load and 90° turn station 14 is illustrated in FIGS. 5A and 5B. The drive mechanism and pushpins 136 of the first collet load station 14 are virtually identical in structure to the drive mechanism and pushpins of the second pushpin turn station 34 and the caplet exit station 52. Moreover, as will be seen with regard to the gelatin dip station 18 illustrated in FIG. 5C, the drive mechanism for the gelatin dip stations 18 and 36 are essentially identical to the basic drive mechanism employed with the pushpin drive mechanisms found at stations 14, 34 and 52.

As shown in FIGS. 5A and 5B, the collet load station 14 is powered by motor 110 connected through a right angle drive 112, a belt 114 and a pulley 116 to a shaft 118 which supports a cylindrical cam 120. Cylindrical cam 120 includes a groove 122 in its surface for driving rotatable cam follower 124 upward and downward. Cam follower 124 is attached to a bracket 126 which carries a plurality of pushpins 136. The drive mechanism is supported by a superstructure 130 mounted on the U-shaped angle support 80 of the machine frame. A pair of slides 132 receives a pair of slidable guideposts 134 which are attached to bracket 126 and provide stability thereto.

Pushpins 136, as illustrated in FIG. 5A are located directly above the caplets 200 held in loading plate 70. Caplets 200 are shown resting on the upper set of split collets 104 in the caplet holding plate 100. FIG. 5A illustrates the loading pins 136 in position prior to the loading of caplets 200 into collet 106.

FIG. 5B illustrates the caplet loading mechanism 12 at the furthest end of its stroke. The pushpins 36 have pushed the caplets 200 through the upper set of collets 104, the plate body 102 and into the second lower set of collets 106 so that they are gripped by the resilient fingers. Slightly more than 50% of the body of each caplet 200 extends beyond the second lower set of collets 106 at this point. This is an important feature because it permits slightly more than half of the body of each caplet 200 to be coated with liquid gelatin. It will be noted in FIGS. 5A and 5B that the loading plate 70 and the caplet holding plate 100 have moved beyond the doctor plate 172, thereby permitting the pushrods 136 to pass all the way into the caplet holding plate 100 without interference.

Next, the pusher 90a will push both plates 70 and 100 from station 14 to station 16 where a pusher 90b will push the loading plate 70 from station 16 to station 56. Of course, during these pushing operations, the entire series of plates 70 and 100 that are abutting are simultaneiously pushed to the next appropriate station. The pusher 90b will therefore push on the plate 70 in station 16 to thereby move the plates 70 in stations 16, 56 and 57 into stations 56, 57 and 58, respectively. Pusher 90f will next push plate 70 in station 58 into station 12 after pusher 90g has been withdrawn, as discussed earlier. As such, loading plates 70 travel in a rectangular plath through stations 12, 14, 16, 56, 57 and 58. The loading plates 70 are loaded in station 12, unloaded in station 14 and returned to station 12 via stations 16, 56, 57 and 58.

The caplet holding plates 100, now being filled with uncoated caplets, next advance to the liquid gelatin dipping station 18 illustrated in FIG. 5C. As previously discussed, the drive train mechanism 110-134 is essentially identical to the drive mechanism described with respect to the pushpin drive stations 14, 24 and 52 and therefore will not be described again in detail.

Dip station 18, illustrated in FIG. 5C, is essentially identical in all respects to the second dip station 36. The caplet holding plate 100 is shown supporting a plurality of caplets 200 held in the downward position. Caplet holding plate 100 itself is supported by a set of upper and lower rollers 128 attached to the movable support bracket 126 which is also steadied by slides 132 and movable guideposts 134 as described with regard to the pushpin mechanism illustrated in FIGS. 5A and 5B.

Caplet holding plate 100, illustrated in FIG. 5C, is shown with the caplets 200 being dipped into a reservoir of liquid gelatin 140 held in the inner pan 62 of the liquid gelatin circulation apparatus illustrated in FIG. 8. The liquid gelatin recirculation apparatus comprises a circular inner pan 62 surrounded by a slightly lower outer circular pan 64. Liquid gelatin 140 forms a meniscus or upper surface into which the caplets 200 are dipped. The coating on the caplets 200 preferably cover slightly more than half of the body of the caplet so as to ensure a complete coating when the reverse side of the caplet is dipped in the second dipping station 36. As shown in FIG. 8, the inner pan 62, which is always filled with gelatin 140, includes a plurality of radially-oriented elongated apertures 220 which communicate between the bottom of the inner pan 62 and the area on the interior of the outer pan 64. An impeller blade 222, supported by bearings 224 and driven by motor 226, drive the gelatin 140 from the bottom of the outer pan 64 through apertures 220 into the upper pan 62. The continual circulation causes the gelatin 140 to spill over the upper edge of the inner pan 62 thereby causing a continual recirculation of the liquid gelatin 128 in the direction of arrows 130. The continual recirculation of the gelatin 140 keeps the gelatin 140 fresh and consistent and therefore substantially improves the equality of the gelatin coating on the caplets 200. The outer pan 64 is mounted on leveling jacks 229 while inner pan 62 is fixed to outer pan 64 via arms 230.

Prior to dipping in gelatin dip stations 18 and 36, the plate 100 is supported above the surface of gelatin 140 in inner pan 62. Rotation of cam 130, driven by motor 110, causes the cam follower 124 to move downwardly causing the caplet holding plate 100 to dip the caplets 200 in gelatin 140. The process is then reversed withdrawing the plate 100 out of the liquid gelatin 140 prior to advancing to the next stage.

In order to get a smooth, uniform coating of gelatin, it is desirable to invert plate 100 so that the dipped gelatin caplets 200 face upward. This is accomplished in flipper station 20 illustrated in detail in FIGS. 7. Flipper station 20, substantially identical to the second flipper station 38, comprises a frame 170 fixed at one side to a joining block and axial portion 182. Flipper frame 170 receives the caplet holding plates 100 when pusher 90a pushes the series of plates 100 in stations 14, 16 and 18.

Initially, the loaded caplet holding plate 100 advances from the dipping station 18 to the flipper station 20. In the process, the pusher mechanism 90a pushes the caplet loading plate 100 into the frame 170 up to the joining block and axial section 182. After the capsule holding plate 100 is securely located in frame 170, the flipper plate drive mechanism 190 causes the frame 17 to rotate 180° as a unit until the caplet loading plate 100 has been inverted into station 22, as shown in phantom lines in FIG. 7, with the still wet gelatin capsules 200 facing in the upward direction. Pusher mechanism 90c then pushes the caplet holding plate 100 sideways out of the frame 170, that is now in station 22, into the drying station 24. After the inverted plate 100 has been discharged in the direction of arrow 188, the flipper mechanism retraces its original 180° rotational route taking it back to its original position in station 20.

After the caplet plate 100 has been inverted in station 20 it is pushed at the second 90° turn station 22 into the beginning of the drying tower 24. The drying tower 24 is substantially identical in structure to the second drying tower 44. Towers 24 and 44 each have a hot air blower 45 (FIGS. 2A and 2B) mounted thereon for supplying dry, heated air to the interiors of towers 24 and 44. Initially, the holding plates 100 proceed into an upward elevator 158 located in station 23 as illustrated in perspective schematic detail in FIG. 6. The first drying tower 24 includes an up station 23, a middle transfer station 26 and a down station 30. The up station 23 and the down station 30 each have a capacity of approximately 10 caplet holding plates 100. Up elevator 158 includes a pair of vertical flighted conveyors 159a and 159b. Each of the vertical conveyors 159a and 159b include belts 160 driven by drive wheels 162. Belt 160 also includes a plurality of flights 164 which contact and carry the body plate 102 of each of the caplet plates 100. The two vertical conveyors 159a and 159b in the up elevator station 23 travel respectively in the direction of arrow 166 thereby causing a caplet holding plate 100 on the bottom to travel up to the top. The caplet holding plates 100 then travel horizontally through the middle transfer section 152 in the direction of arrow 156, under the control of pusher 90h, until it comes into position on the top of the down elevator station 30. The two conveyors 159c and 159d in the down elevator station 30, travel in the direction of arrow 167, thereby causing caplet holding plate 100 to travel from the top to the bottom. Finally, the caplet holding plate 100 travels horizontally out of the drying tower 24 into the series of dead stations 32 under the control of pusher 90k.

While the caplet holding plates 100 and the caplets 200 travel through the drying tower 24, they are exposed to forced hot air from hot air blowers 45 for a period of approximately 20 minutes during which time the liquid gelatin 140 drys. From there the dried gelatin capsules, facing upward in plates 100, travel along a series of dead stations 32 to the second caplet pushpin mechanism and the third 90° turn mechanism at station 34.

The operation between stations 14 and 32 is essentially identical to the operations that take place between stations 34 and 50. Namely, the caplets 200, facing upward, are pushed downwardly through the caplet holding plate 100 until the previously undipped end of the capsule 200 emerges through the resilient fingers on each of the collets 104 in the plate. This operation is substantially identical to that shown in FIG. 5B except that collets 104 now face downwardly and collets 106 now face upwardly.

The caplet holding plate 100, under the control of pusher 90d, then travels through a dead station 60 to the second dipping station 36 where the undipped half of the gelatin capsule is dipped in gelatin 140 in the same manner as illustrated in FIG. 5C. The capsule holding plate 100 next travels to the second flipper station 38 where it is flipped into station 40 in the manner described previously with respect to FIG. 7. A fourth 90° turn mechanism, having pusher 90e, located at station 40 pushes the still wet, upwardly facing caplets 100 into the second drying tower station 44. Stations 42 and 50 comprise the up and down elevators of the second drying tower station 44. The dried gelatin capsules, still facing upward emerge onto exit station 51. At exit station 51, a third multiple pin mechanism, similar to that illustrated in FIG. 5A, pushes the completely coated and dried caplets 200 through collets 106 and 104 and out into a collection bin located underneath. From there the coated caplets 200 travel to a suitable bottling, labeling and packaging section known to those of ordinary skill in the art. The caplet holding plates 100 are then moved into station 12 to repeat the process.

While the invention has been described with reference to the preferred embodiment thereof, it will be understood by those of ordinary skill in the art that modifications can be made to the apparatus without departing from the spirit and scope of the invention as a whole.

We claim:

1. An apparatus for holding caplets for dipping in gelatin comprising:
   a plate having a plurality of apertures therein arranged in a two-dimensional array of rows and columns, said plate having a first and a second side;
   a first set of collets mounted on said first side of said plate and having apertures therethrough; and,
   a second set of collets mounted on said second side of said plate and also having apertures therethrough;
   wherein said apertures in said first set of collets and said second set of collets are aligned and communicate with each other through the apertures in said plate such that caplets held by said first set of collets can be dipped in gelatin and simultaneously pushed through said plate to be held by said second set of collets for dipping in gelatin.

2. The apparatus of claim 1 wherein said collets have resilient fingers thereon for gripping a caplet.

3. A caplet holding apparatus for use in coating a caplet with gelatin comprising:
a holding plate having apertures therethrough, said holding plate including a first side and a second side;
a first set of collets mounted on said first side of said holding plate and having apertures therethrough which are aligned with and communicate with the apertures in said holding plate;
a second set of collets mounted on said second side of said holding plate and also having apertures aligned with the apertures in said holding plate and said second set of collets, said collets comprising split collets having resilient fingers thereon for gripping a caplet, said first and second set of collets being arranged in rows and columns on said plate so as to form a two dimensional array;
a loading plate mounted above said holding plate and having a plurality of loading holes therein arranged in a two-dimensional array of columns and rows for receiving caplets randomly deposited thereon;
a retaining plate means located directly below said loading plate for retaining said caplets in said loading holes until such time as they are ready for loading into said collets;
transport means for moving said loading plate and said holding plate beyond said retaining plate means so that said caplets can extend from said loading holes and rest on said collets; and
loading transfer means for pushing said caplets simultaneously into said first set of collets.

4. An apparatus for coating a caplet with gelatin comprising:
a caplet holding means having a first side and a second side each side including a first and a second set of caplet gripping means thereon;
a first gelatin dipping bath for coating caplets held by said first set of caplet gripping means;
first drying means for drying caplets held by said first set of caplet gripping means after said caplets have been dipped in said first gelatin dipping bath;
first flipping means for flipping said caplet holding means after it has passed through said first drying means;
transfer means for transferring caplets held by said first set of caplet gripping means to said second set of caplet gripping means;
a second gelatin dipping bath for coating said caplets held by said second caplet gripping means;
second drying means for drying said caplets held by said second caplet gripping means after said caplets have passed through said second gelatin dipping bath; and
wherein said caplet holding means comprises:
a plate having apertures therethrough, said plate including a first side and a second side;
a first set of collets mounted on said first side of said plate and having apertures therethrough which are aligned with and communicate with the apertures in said plate; and
a second set of collets mounted on said second side of said plate and also having apertures aligned with the apertures in said plate and said second set of collets, wherein said transfer means pushes caplets held by said first set of collets through said aperture in said plate and into said second set of collets, said collets comprising split collets having resilient fingers thereon for gripping a caplet, said first and second set of collets being arranged in rows on said plate so as to form a two dimensional array; and
a feeder means for feeding caplets to said caplet holding means, said feeder means comprising:
a hopper for holding uncoated caplets;
a loading plate means located underneath said hopper and having a plurality of loading holes therein for receiving caplets from said hopper;
a retaining plate located below said loading plate means to retain said caplets in said loading holes until such time as they are ready for loading into said caplet holding means;
transport means for moving said loading plate means and said caplet holding means beyond said retaining plate so that said caplets can extend from said loading holes and rest on said collets; and
loading transfer means for pushing said caplets into said first set of collets.

5. The apparatus of claim 4 wherein the loading holes comprise tapered apertures which are wider on the side of said loading plate means that faces said hopper and narrower on the side of said loading plate means which faces said caplet holding means.

6. The apparatus of claim 5 further comprising:
caplet exit transfer means for pushing caplets out of said second set of collets after said caplet holding means has passed through said second drying means.

7. The apparatus of claim 6 wherein said first and second dipping means comprise:
a first pan for containing liquid gelatin material;
a second pan located inside said first pan and communicating therewith through apertures in the bottom thereof; and
impeller means located in said first pan underneath said second pan for propelling gelatin through the apertures in the bottom of said second pan and out over the edges of said second pan back into said first pan.

8. The apparatus of claim 7 further comprising:
a second flipper means for flipping said caplet holding means, said second flipping means being located between said second dipping means and said second drying means.

9. The apparatus of claim 8 wherein said first and second drying means each comprise:
an up section means for conveying caplet holding plates upwardly;
a down section means for conveying said caplet holding plates downwardly after they have passed through said up section means; and
heating means for providing hot air to said first and second drying towers.

10. A method of coating caplets comprising:
randomly feeding uncoated caplets onto a first surface;
orienting a set of said caplets on said first surface into a two-dimensional array;
moving said set of said caplets into a set of collets with a portion of each said caplet extending from said collets and with said collets arranged as a two-dimensional array on a plate;

dipping the exposed portion of said caplets into a liquid bath to coat said caplets;

drying said caplets to form a dry coating on said caplets;

moving said caplets in said collets to expose an uncoated portion of said caplets;

dipping the uncoated portions of said caplets into a liquid bath to coat said caplets;

drying said caplets to form a dry coating on said caplets; and moving said caplets out of said collets.

11. A method according to claim 10 wherein said liquid bath is gelatin.

* * * * *